United States Patent [19]

Bodicky

[11] Patent Number: 5,240,537
[45] Date of Patent: Aug. 31, 1993

[54] METHOD FOR MANUFACTURING A SOFT TIP CATHETER

[75] Inventor: Raymond O. Bodicky, Oakville, Mo.

[73] Assignee: Namic U.S.A. Corporation, Glens Falls, N.Y.

[21] Appl. No.: 724,303

[22] Filed: Jul. 1, 1991

[51] Int. Cl.⁵ .............................................. B29C 65/02
[52] U.S. Cl. ............................... 156/244.13; 156/258;
  156/304.2; 156/304.5; 156/304.6; 156/309.6;
  264/162
[58] Field of Search ................ 264/162, 173; 156/158,
  156/258, 244.13, 304.2, 304.5, 304.6, 309.6;
  604/280

[56] References Cited

U.S. PATENT DOCUMENTS

| | | | |
|---|---|---|---|
| 1,998,633 | 4/1935 | Nichols | 156/304.2 |
| 2,914,438 | 11/1959 | Sandt et al. | 156/283 |
| 3,485,234 | 12/1969 | Stevens | 604/282 |
| 3,719,737 | 3/1973 | Vaillancourt et al. | 264/162 |
| 3,972,548 | 8/1976 | Roseen | 285/381 |
| 3,998,682 | 12/1976 | Harmsen | 156/304.5 |
| 4,092,193 | 5/1978 | Brooks | 156/83 |
| 4,282,876 | 8/1981 | Flynn | 128/349 |
| 4,385,635 | 5/1983 | Ruiz | 604/280 |
| 4,531,943 | 7/1985 | Van Tassel et al. | 604/280 |
| 4,551,292 | 11/1985 | Fletcher et al. | 264/139 |
| 4,596,563 | 6/1986 | Pande | 604/264 |
| 4,636,272 | 1/1987 | Riggs | 156/158 |
| 4,636,346 | 1/1987 | Gold et al. | 264/139 |
| 4,834,726 | 5/1989 | Lambert | 604/281 |
| 4,886,506 | 12/1989 | Lougren et al. | 604/280 |
| 4,963,442 | 9/1989 | DeMello | 604/282 |
| 5,017,259 | 5/1991 | Kohsai | 156/304.2 |
| 5,085,649 | 2/1992 | Flynn | 604/282 |
| 5,120,323 | 6/1992 | Shockey et al. | 604/282 |

FOREIGN PATENT DOCUMENTS

| | | |
|---|---|---|
| 0417865 | 3/1991 | European Pat. Off. . |
| 0136719 | 7/1979 | Fed. Rep. of Germany ...... 156/158 |
| 2535337 | 11/1982 | France . |
| 55-139217 | 10/1980 | Japan ............................... 156/304.2 |

Primary Examiner—Jay H. Woo
Assistant Examiner—Robert B. Davis
Attorney, Agent, or Firm—Kenyon & Kenyon

[57] ABSTRACT

A catheter and a method of manufacture of a catheter which includes a relatively rigid body and a relatively soft tip for decreasing the likelihood of injury or damage to tissue such as the wall of a blood vessel or the heart when the catheter is used as a part of an invasive medical procedure such as angiography or angioplasty. The method includes the use of a core material which is sufficiently resistant to high temperatures to allow extrusion of catheter material thereover in the process of forming the catheter. The core controls the catheter's inside diameter, and is sufficiently heat resistant to allow its use through all subsequent manufacturing process steps involving the formation of the soft tip. The method of the present invention prevents foreign material build up within the inner diameter of the catheter during processing, eliminates the need for special fusion support mandrels during fusion of the soft tip onto the catheter, and maintains the integrity of the internal diameter of the catheter and soft tip during the thermal and pressure processes of the manufacture. The invention also includes a novel method of sizing and fusing the soft tip onto the catheter including the use of a piston member about the core which can apply pressure to the material forming the soft tip at any time before, during or after the thermal heating step.

32 Claims, 3 Drawing Sheets

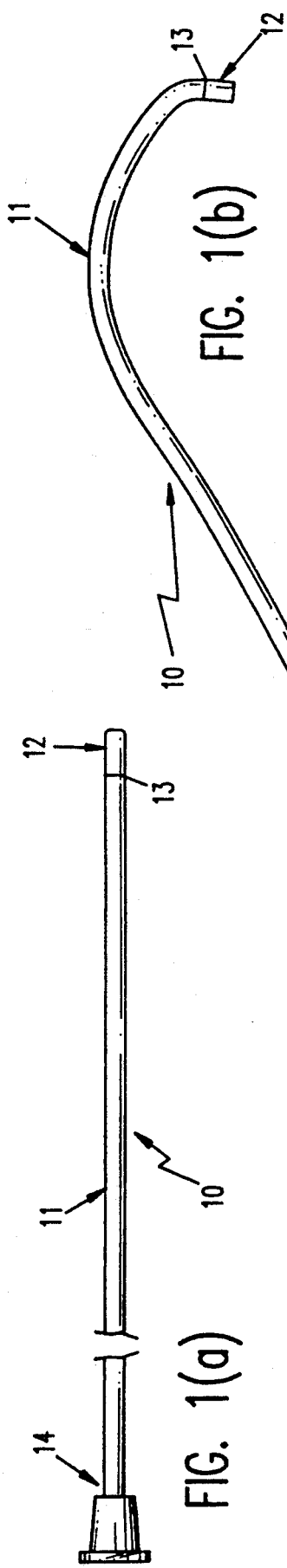
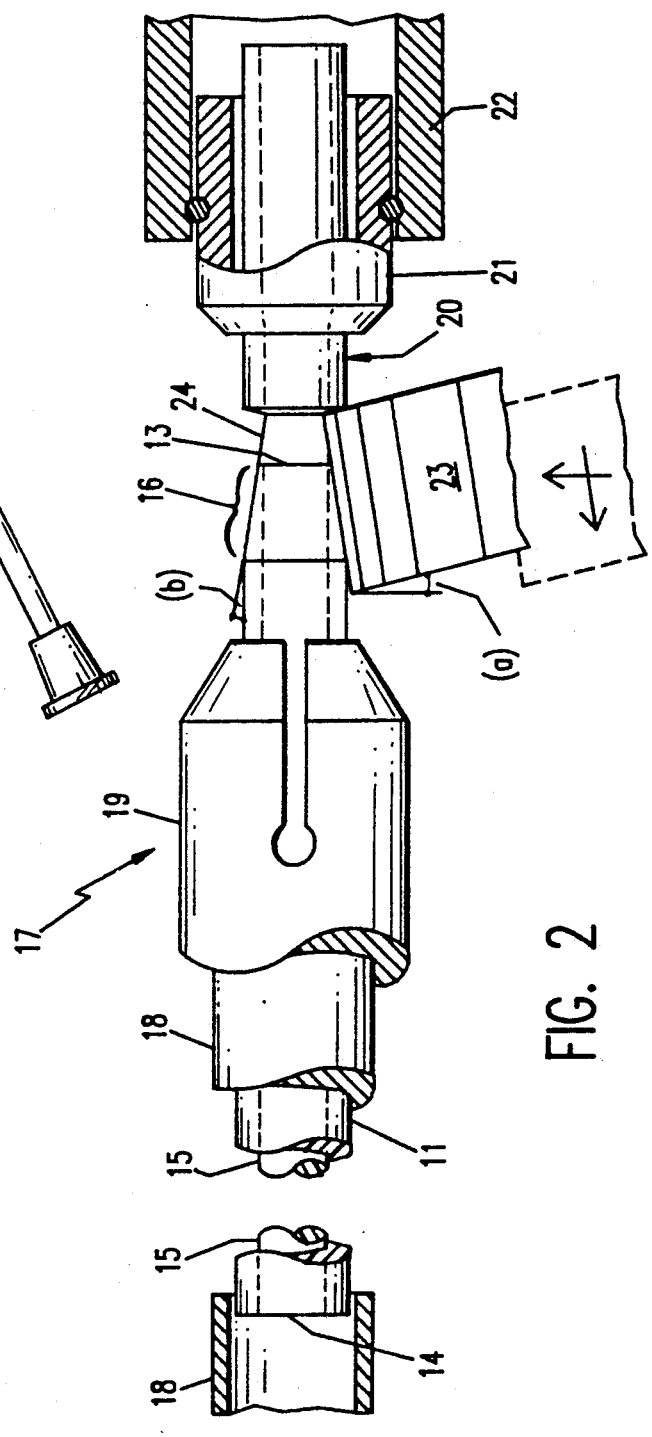
FIG. 1(a)
FIG. 1(b)
FIG. 2

METHOD FOR MANUFACTURING A SOFT TIP CATHETER

BACKGROUND OF THE INVENTION

1. Field of the Invention

The invention relates generally to catheters and methods of manufacture thereof which include the formation of a relatively soft tip onto a relatively rigid catheter body. More specifically, the invention relates to catheters useful for insertion into a living body for performance of medical procedures, such as angiography and guiding catheters for use in angioplasty procedures and other therapeutic and/or diagnostic procedures, and methods of manufacturing the catheter, specifically including methods of forming the soft tip thereon.

2. Brief Description of the Prior Art

It is common for many surgical procedures to include the insertion of a catheter into a living body. In some instances, such as during angiography or angioplasty procedures, it is common to insert a catheter long distances through vessels which are formed of fragile vascular or heart wall tissue which can be easily damaged or even pierced by the catheter during the insertion process if extreme care is not taken. Catheters used for such purposes must be sufficiently rigid to be advanced long distances through a vessel (by pushing from the proximal end thereof), and able to resist twisting or torque forces. Often, such catheters must be performable into a particular shape corresponding to a particular vessel pathway through which it must pass, and/or be able to withstand high fluid pressures during use.

Because these catheters are of necessity formed of a relatively rigid material, the distal tip thereof can be very destructive to the delicate vessel wall tissue through which the catheter passes. A catheter with a rigid distal tip can severely damage a vessel or heart wall, and although rare, may actually pierce through to the exterior of the tissue wall causing severe trauma to the patient or even death.

This problem has been addressed in the past by forming the distal end of the relatively rigid catheter with a relatively soft tip which is either non-traumatic or significantly less traumatic to vessel wall tissue than the relatively rigid material forming the body of the catheter. A catheter having a soft tip which is exemplary of the prior art is disclosed in U.S. Pat. No. 3,485,234 to Stevens, and U.S. Pat. No. 4,636,272 to Riggs.

Catheters have been formed in prior art manufacturing procedures by extruding catheter material over an elongated cylindrical core having a uniform diameter which ensures that the resultant catheter is formed to a uniform inner diameter. The catheter is then removed from the core or the core is stretched to reduce its diameter for purposes of later removal, and a distal end of the catheter is prepared to receive a relatively soft tip, either by chemical bonding such as adhesion, or by thermal bonding such as fusion of a soft tip material to the distal end of the catheter.

If fusion is used to join the soft tip to the catheter, a fusion rod may be inserted through the soft tip and the catheter, and heat is applied at the interface of the soft tip and the catheter distal end in order to fuse the materials together. Once cooled, the fusion rod and/or core is then removed and the soft tip is trimmed to the desired length.

It has been difficult to maintain a constant uniform internal and external diameter throughout the entire length of the catheter body/soft tip interface using the prior art processes of manufacture. Also, it has often been difficult to eliminate foreign material build up within the internal diameter of the catheter during the tip formation phase of the manufacturing process. Further, when heat is used to bond the materials together at the catheter body/soft tip interface, it has often been necessary to insert a fusion rod into the already formed catheter and soft tip in order to help maintain the desired internal diameter during the fusion and cooling processes.

There therefore exists a need in the art to develop a relatively rigid catheter having a relatively soft tip which is formed of a uniform internal diameter across the catheter body/soft tip interface. There is further a need in the art to develop a manufacturing process which includes heat fusion of a soft tip to a relatively rigid catheter body, which eliminates the need for a special fusion rod to be inserted through the catheter and soft tip thereof as part of the fusion process.

OBJECTS AND SUMMARY OF THE INVENTION

It is an object of the present invention to provide a catheter formed with a relatively soft tip at the distal end of a relatively rigid body which is useful in conjunction with various medical procedures.

It is another object of the present invention to provide a method of manufacturing a catheter as described above which includes the use of a core in the formation of the catheter body to control the interior diameter of the catheter body, and which is also utilized during subsequent steps of the manufacturing process to attach the soft tip to the distal end of the catheter body, and to match the internal diameter thereof with the internal diameter of the catheter body.

It is another object of the present invention to provide a manufacturing process as described above in which the soft tip is formed to the distal end of the catheter body by the combination of fusion and pressure.

It is also an object of the present invention to provide a manufacturing method for the catheter described which further includes heating and compressing a predetermined volume of material about the core in order to form the soft tip to its desired length and shape simultaneously with the fusion thereof to the distal end of the catheter body.

These and other objects of the present invention are realized in a preferred embodiment of a catheter and a method of manufacturer thereof, which includes an elongate catheter body having a proximal and a distal end formed of a relatively rigid material and a soft tip formed on a distal end of the relatively rigid catheter body which reduces the likelihood of damage to wall tissue as a result of use of the catheter during medical procedures. A preferred method of manufacture of the catheter, described for purposes of illustration and not for purposes of limitation, includes the use of an elongate core having a predetermined diameter over which material forming the elongate body of the catheter is extruded, the outer diameter of the core functioning to form and control the interior diameter of the catheter body. In a further step of the manufacturing process, the core with the catheter body extruded thereover is sized and placed in a rotating apparatus to form a tapered distal end thereon. The taper may be formed by applying a grinding wheel to the catheter body while the catheter body is being rotated relative thereto. The core is then broken away from its fixed position within the catheter body and extended slightly beyond the taper on the distal end thereof. A predetermined volume of tubularly shaped material (which will eventually become the soft tip) is then placed over the extended portion of the core, and a sleeve is placed over the material and the distal end of the catheter body, including the taper. A hollow piston is then slid over the core to trap the volume of material between the piston and the taper on the distal end of the catheter body. The entire assembly is then placed in a heating apparatus and heated until the volume of material either softens, or reaches its melting point as desired. The piston is then moved in the direction of the distal end of the catheter body by means of a push cylinder, causing the heated volume of material to be fused to the distal end of the catheter body and simultaneously formed into its desired length and shape by the pressure of the piston. The entire assembly is then cooled and the catheter body, (including the soft tip fused thereto) is removed from the sleeve and piston with the core remaining in place. A stripping sleeve is then placed over the soft tip and distal end of the catheter and used to separate the core from the completed catheter. The catheter may then be formed into a specific shape as desired depending upon the intended use thereof.

The above and other objects and advantages of the present invention will become apparent to those skilled in the art upon review of the following detailed description of the preferred embodiments, especially when considered in conjunction with the accompanying drawings in which like numerals refer to similar elements in each of the several figures.

DETAILED DESCRIPTION OF THE DRAWINGS

FIG. 1(a) is a perspective view of a preferred embodiment of the catheter made in accordance with the principles of the present invention;

FIG. 1(b) is a perspective view of the catheter of the present invention formed for use as an angiography or guiding catheter;

FIG. 2 is a partial cross-sectional, partial cut away view of one phase of the preferred manufacturing process of the present invention;

DETAILED DESCRIPTION OF THE PREFERRED EMBODIMENTS

Figure 3A:
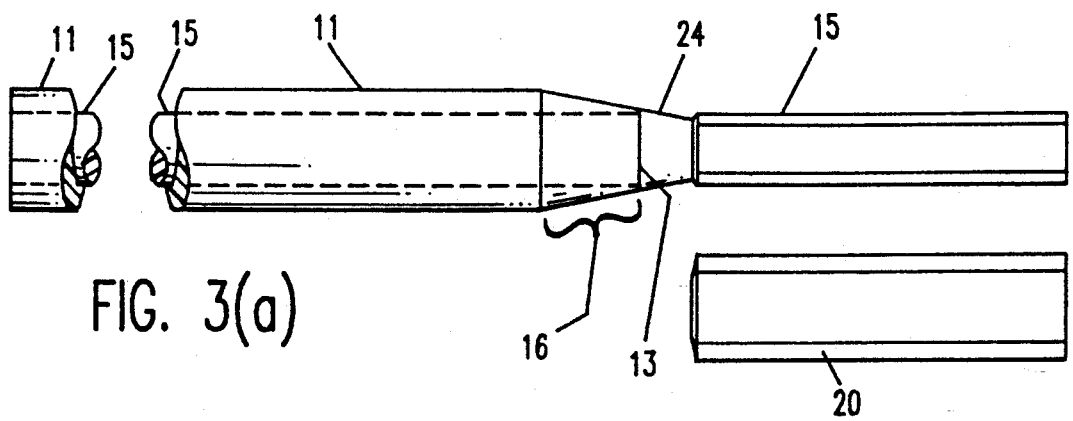
FIG. 3(a) is a side view of the core and catheter body of the present invention after completion of the manufacturing process shown in FIG. 1.

In the exemplary drawings, used for purposes of illustration only and not by way of limitation, an embodiment of a catheter made in accordance with the principals of the present invention is referred to generally by the reference numeral 10. As shown specifically in FIGS. 1(a) and (b), the catheter 10 is formed generally of an elongate relatively rigid tubular catheter body 11 having a distal end 13 and a proximal end 14, and a relatively soft tip 12 permanently attached to distal end 13. The complete catheter 10 therefore includes the rigid catheter body 11 and the soft tip 12.

In its finished form, catheter 10 may be relatively straight along its entire length as shown by FIG. 1(a), or alternatively may be permanently configured into a variety of shapes corresponding to the needs of a particular medical procedure. For example as shown in FIG. 1(b), the body 11 may be formed to take the shape of a flow path through vessels in or near the heart for purposes of convenience in placement of the catheter therethrough during an angioplasty procedure. Although a catheter formed in accordance with the principles of the present invention may be useful for a variety of medical or surgical procedures, the embodiment particularly shown in the drawings of the present disclosure illustrate a catheter which is intended for use in angioplasty or angiography procedures. The disclosed embodiment is chosen for ease of explanation of the invention and is not intended to limit the scope thereof.

FIGS. 2 through 6 illustrate in a generally chronological manner, the more important phases of the manufacturing process of the present invention, and the method of manufacturing the catheter of FIG. 1(a) will be described in conjunction therewith. It should be remembered however that the manufacturing process as described herein can be used to manufacture catheters intended for use in a variety of medical procedures wherein a soft tipped catheter may be advantageous.

Prior to the specific inventive phases of the manufacturing method of the invention, the catheter body 11 may be initially formed by extruding a catheter material over the core 15 in any one of a variety of well known processes. The core 15 of the present invention may be formed of any semi-rigid, yet pliable alloy, composite, metal or polymer, which has the ability to maintain its dimensional integrity during subsequent high temperature processes. It is preferred that the core 15 contain, either within its composition, or as a surface coating, a low friction material which will allow it to be easily removed from the catheter 10. Examples of such materials may be lubricants such as silicone oils, or paraffinic polymers such as, polytetrafluoroethylene (PTFE), etc. For example, if the catheter 10 is intended to be used to pass other medical instruments therethrough into particular locations in a patient's body, a low friction interior surface is desirable. Therefore, a low friction material such as PTFE should be coated (e.g., sprayed, dipped, extruded, etc.) in a thin film over the core 15 prior to extrusion of the catheter body material thereover. The PTFE film should be etched or adhesively coated over its entire exterior surface to allow the film to bond to the extruded catheter material and be removed with the catheter 10 when the catheter 10 is stripped away from the core 15.

Alternatively, if the catheter 10 has no need of a low friction interior surface, the core 15 may be formed of a lubricious material such as acetal, or it may be prepared, such as by roughing the surface thereof and/or placing an adhesive thereon and coated with PTFE, to bond the film and the core 15. The film should not be etched or adhesively coated in this instance, so that when the core 15 is stripped from the catheter 10, the film will remain attached to the core 15. If lubricated grades of acetal (e.g., DELRIN TM, CELCON TM, etc.) are used as material for the core 15, there is no need for the above exterior coating treatment.

Referring now to FIG. 2, in which the initial phase of the unique manufacturing process is depicted, the core 15 with the catheter body 11 thereover, is cut to the desired length and then placed within a lathe type rotation apparatus (indicated generally as 17) in preparation for grinding a taper 16 on the distal end 13 of the body 11. The proximal end 14 of the catheter body 11 is placed through a rotating support cylinder 18 and clamped in position by the rotating collet 19 so that a predetermined length of the catheter body 11 extends from the collet 19. The extension 20 of the catheter body 11 (which becomes waste or "of fal" as will be explained momentarily) is placed in a slip fit type live-center support 21 which is subsequently mounted in a tail stock support 22. Once the catheter body 11 is in place, the lathe 17 is engaged to rotate the core 15 and catheter body 11 about their longitudinal axis.

Next, a rotating grind wheel 23 moves from a first position (shown in dotted lines) where it rests while the catheter body 11 and core 15 are being loaded into the lathe 17, to a second position in which it grinds completely through the catheter body 11 and partially through the core 15 to form taper 16 and notch 24 respectively. The grinding wheel 23 is set at a predetermined angle to generate the angle (a) of the taper 16. Although an angle (a) of approximately 30 degrees is preferred in the present embodiment, angles ranging anywhere between approximately 15 and 45 degrees are preferred in the present invention. Further, if necessary to grind the desired taper 16, the grinding wheel 23 may be traversed longitudinally along the catheter body 11. Also, it may be desirable during the grinding process to support the core 15 and/or catheter body 11 at a position directly opposite the grinding wheel 23, especially if long tapered surfaces are being formed, or extremely flexible core material is being used, in order to prevent the core 15 and catheter body 11 from bowing during the grinding process due to pressure exerted by the grind wheel 23.

Figure 3B:
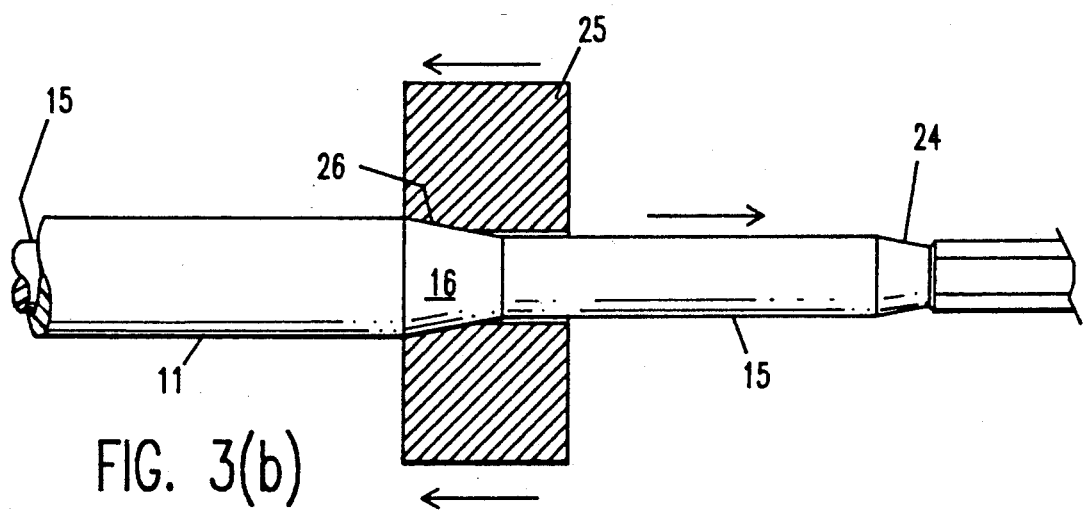
FIG. 3(b) is a perspective view of the catheter body and core of the present invention used in conjunction with apparatus (shown in cross-section) for extending the core beyond the catheter body distal end.
Figure 3C:
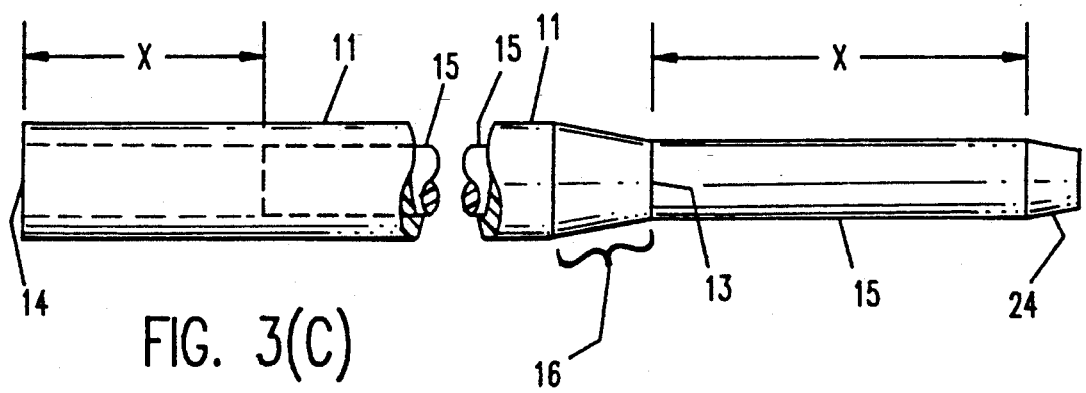
FIG. 3(c) shows the catheter body and core prepared for the next phase of the manufacturing process.

As shown in FIG. 3(a), once the taper 16 is formed at the distal end 13 of the catheter body 11, the entire catheter body 11 and core 15 are removed from the lathe 17, and the "of fal" 20 is removed from the core 15 and discarded. As shown in FIG. 3(b), the core 15 is then advanced distally out of the catheter body 11 through the help of a female conical bushing 25 which includes conical opening 26 for matching the taper 16. The bushing 25 is slipped over the core 15 until its opening 26 interfaces the taper 16 and holds the catheter body 11 in place while the core 15 is drawn in the distal direction. As shown in FIG. 3(c), the core 15 is withdrawn in this manner to a predetermined distance (x) from the distal end 13 of the catheter body 11. The portion of the core 15 which is distal of notch 24 may then be trimmed off if desired in preparation for the next (fusion) phase of the manufacturing process. The preferred distance (X) in the shown embodiment is approximately 1¼ inches, although it may be within the range of 1 to 1½ inches. The distance (X) for other embodiments of the present invention of course may vary greatly from the shown embodiment.

It is important to note that the advancement of the core 15 a distance (X) out of the catheter body 11 effectively overcomes any initial resistance of movement between the core 15 and the catheter body 11. Breaking the catheter body 11 and core 15 apart from an incidental bonding therebetween which may have occurred, either intentionally or unintentionally, as a result of an initial extrusion process (if such occurred), renders removal of the core 15 after fusion of the soft tip 12 (explained in detail below) much easier to accomplish and results in much less stress applied to the catheter body/soft tip interface.

Figure 4:
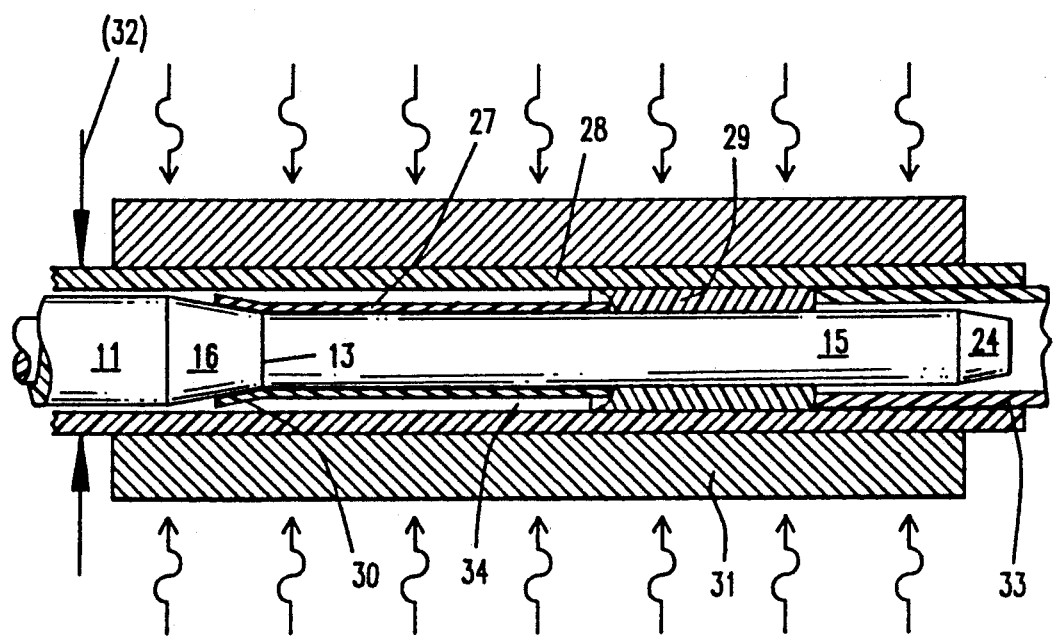
FIG. 4 is a partial cross-sectional view of a phase of the manufacturing process subsequent to that shown in FIG. 3(c) and prior to fusing the soft tip to the catheter body.

As best shown in FIG. 4, a volume of material, identified in this process step only as element 27, and which will eventually constitute the soft tip 12 of the catheter 10, is inserted over the core 15 until it contacts the distal end 13 of the catheter body 11, and preferably until an end 30 thereof is forced to slide partially over at least a small portion of the taper 16. The tube 27 preferably has an inner diameter which is only slightly larger than the outer diameter of core 15, and an outer diameter which is smaller than the outer diameter of the catheter body 11. As is readily evident, the thickness and length of the material 27 may vary to allow a predetermined total volume of material to be inserted over the core 15. The total volume of material included in tube 27 is precalculated to result in a soft tip 12 formed to its desired finished length as will be explained in more detail below.

A sleeve 28, preferably formed of PTFE is then slid over the entire extended portion of the core 15 and continues to extend over the taper 16 and a portion of the catheter body 11. A piston 29 is then inserted over the core 15 to abut against the tube 27. At this point, the volume of material 27 is completely enclosed within a generally annular chamber 34 defined by the outer surface of core 15, the proximal end of piston 29, the interior surface of sleeve 28 and the taper 16 of the catheter body 11. The expanded end 30 of the tube 27 is preferably expanded to a diameter which is slightly smaller than the inside diameter of the sleeve 28.

The above completed assembly is then slid into the containment bushing 31 of a fusion machine (not shown) to a predetermined depth, and a clamp (shown by arrows 32) is activated to hold the assembly at the predetermined depth during the fusion process. Next, a push cylinder 33 is inserted over the core 15 into abutting relationship with piston 29, so as to be usable to force piston 29 against tube 27 to compress the tube 27 in the direction of the taper 16.

The fusion machine is then activated, causing the containment bushing 31 thereof to be heated to a temperature which exceeds the melting point of the material of tube 27. At the activation of the fusion machine, the push cylinder 33 may be immediately moved toward push piston 29 to compress tube 27 toward the taper 16. Alternatively, movement of cylinder 33 may be delayed a period of time to allow the tube 27 to become heated, or even, further delayed until the tube 27 reaches its melting point and begins to "wick" up the taper 16, prior to becoming compressed by the piston 29.

As the material of tube 27 melts, and the piston 29 moves towards taper 16, a portion of the melted material of tube 27 interfaces and fuses with the taper 16 while the remainder thereof is formed into the shape of the chamber 34. The material 27 thus is formed to the same inner and outer diameters as the catheter body 11, due to the restrictions of the core 15 and the sleeve 28 respectively.

Figure 5:
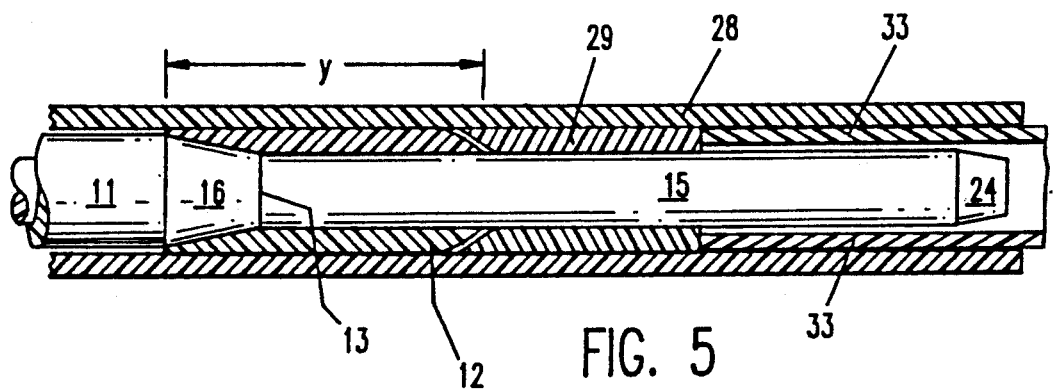
FIG. 5 is a partial cross-sectional view showing the soft tip fused to the catheter body.

As best shown in FIG. 5, once the piston 29 has moved toward taper 16 to force the material of tube 27 to completely fill the chamber 34 therebetween, the assembly is gradually removed from the containment bushing 31 in order to allow cooling to occur slowly in the initial stages thereof in order to avoid bulging or misshaping of the melted material due to rapid withdrawal. Once the assembly has cooled sufficiently to remain in tact when it is completely withdrawn from the bushing 31, it is rapidly cooled. The resultant length (y) of the fused soft tip 12 can be predetermined by calculating the volume of the chamber 34 at the end of the fusion/compression process step. This of course can be done in a straightforward manner by calculating the desired volume to be occupied by soft tip 12 at the completion of the fusion process and inserting the proper volume of material 27 into the chamber 34 which will yield the predetermined volume (and thus the predetermined length) after fusion. Since the inner and outer diameters of the sleeve 28 and core 15 respectively remain constant, any change in the volume of material 27 results directly in a corresponding change in the length of the finished soft tip 12. In the shown embodiment of the invention, the length of the soft tip 12 is preferably approximately ¼ inch. However, soft tip lengths may vary greatly with other possible embodiments.

Figure 6:
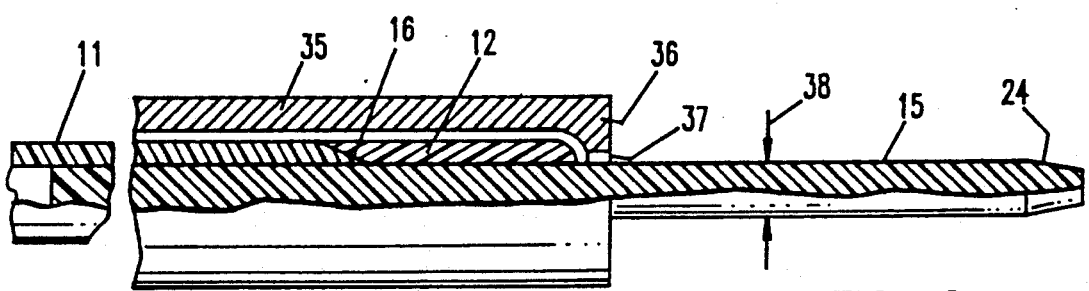
FIG. 6 is a partial cross-sectional view of the completed catheter, including apparatus used to remove the core therefrom.

Once the assembly has cooled, the sleeve 28, piston 29, and push cylinder 33 are removed, leaving only the completed catheter 10 surrounding the core 15. As shown in FIG. 6, a stripping sleeve 35 is then inserted over the core 15 in preparation for stripping the core 15 from the catheter 10. The sleeve 35 has an inner diameter which is slightly larger than the outer diameter of the catheter 10, except at the distal end 36 thereof which is formed into a shoulder 37 which forms a circular opening which is of a diameter less than the outer diameter of the catheter 10, yet slightly greater than the outer diameter of the core 15. The exposed portion of the core 15 is clamped (as shown by element 38) and the core 15 and the sleeve 35 are moved in opposite directions resulting in the catheter 10 being stripped from the core 15.

Once the catheter has been stripped from the core 15, it is essentially complete in its manufacture. However, should it be desired, the catheter may be subjected to finishing processes such as burr removal, trimming to length of the catheter body 11, tip molding, etc. Further, the catheter body 11 and soft tip 12 may be permanently shaped into a desired configuration such as shown in FIG. 1(b) to allow the catheter to be used for particular surgical procedures such as angiography, angioplasty or the like.

As is evident in the above explanation of the preferred method of manufacture of the present invention, it is important that the materials forming the various components of the sleeve 28, piston 29, and core 15, be chosen to have higher melting points than the material forming the soft tip 12. This of course is necessary in order that fusion will be able to occur at melting of the tubular material 27, prior to any of these other components reaching their melting point. It may however be desirable for certain purposes to form the catheter body 11 and soft tip 12 of an identical or similar material having the same melting point for each yet having different durometer hardnesses.

Although the invention is not intended to be limited by the particular materials used, it is suggested that in the preferred embodiment of the present invention, the soft tip 12 of the catheter 10 be formed of a relatively soft material such as a polymer having a low melting point. An example of an acceptable material would be polyurethane. If polyurethane is used, material used to form the sleeve 28, the piston 29, and the core 15 are preferably materials having higher melting points than polyurethane. For example, the catheter body 11 may be formed of a high melting point polymer such as nylon. The sleeve 28 and piston 29 may be formed of high melting point polymers such as PTFE or the like. The core 15 may be formed of any semi-rigid lubricious yet pliable alloy, composite, metal or polymer material which is capable of maintaining its dimensional integrity during the heating and cooling processes of the invention. An example of a preferred material would be acetal. In this example, heating temperatures would preferably be within the range of 380 to 430 degrees Farenheit, and more preferably approximately 410 degrees Farenheit. Further, the pressure exherted by the piston 29 in the example embodiment would preferably range from 0.3 to 1.5 psi.

It is to be understood that the above embodiments of the present invention, including specified limitations thereto, are intended to be only illustrative of the concepts of the present invention. Various modifications or alternative arrangements or embodiments may be devised by those skilled in the art without departing from the spirit and scope of the present invention, and it is intended that the present invention be limited only by the appended claims.

What is claimed is:

1. A method of manufacturing a soft tipped catheter including the steps of:
   a) providing a core having a catheter body located thereover,
   b) forming a distal end of the catheter body with a taper,
   c) advancing the core a predetermined distance within the catheter body,
   d) inserting a sleeve over a portion of the catheter body including the taper of the catheter body and a portion of the advanced length of the core,
   e) inserting a predetermined volume of material within the sleeve and about the advanced length of the core,
   f) forming a soft tip on the catheter body at the taper thereof from the volume of material by inserting a piston within the sleeve and over the advanced length of the core such that a chamber is formed by the taper, the sleeve, the core, and the piston, and the predetermined volume of material for forming the soft tip is located within the chamber, and
   g) removing the core.

2. A method according to claim 1 wherein said step of forming a taper on the catheter body includes grinding the taper to a predetermined angle.

3. A method according to claim 2 wherein said step of grinding the taper also includes grinding a notch into the core.

4. A method according to claim 1 wherein said step of forming a soft tip further includes applying pressure to the predetermined volume of material by forcing the material against the taper of the catheter body with the piston.

5. A method according to claim 4 wherein said step of forming a soft tip further includes applying heat to the predetermined volume of material.

6. A method according to claim 5 wherein said step of applying pressure to said predetermined volume of material occurs prior to said step of applying heat to said predetermined volume of material.

7. A method according to claim 5 wherein said step of applying pressure to said predetermined volume of material occurs during said step of applying heat to said predetermined volume of material.

8. A method according to claim 5 wherein said step of applying pressure to said predetermined volume of material occurs after said step of applying heat to said predetermined volume of material.

9. A method according to claim 1 wherein said step of forming a taper on the catheter body includes forming a taper having an angle relative to the longitudinal axis of the catheter body of between 15 and 45 degrees.

10. A method according to claim 2 wherein said step of grinding a taper includes the use of a grinding wheel and a rotation apparatus, the catheter body and core being held and rotated by the rotational apparatus and the grinding wheel being used to form the taper on the catheter body.

11. A method according to claim 10 in which the grinding wheel is movable from a first position in which the catheter body and core are attachable to the rotation apparatus, and at least a second position in which the grinding wheel is in contact with the catheter body for grinding the taper.

12. A method according to claim 1 wherein said step of forming a soft tip on the catheter body includes forming the soft tip of an outer diameter equal to the outer diameter of the catheter body and of an inner diameter equal to the inner diameter of the catheter body.

13. A method according to claim 1 wherein the resultant length of the soft tip is predetermined by the initial volume of material used in said forming step.

14. A method according to claim 1 wherein said step of forming a soft tip includes changing the shape of the predetermined volume of material.

15. A method according to claim 1 wherein the catheter body is formed of nylon.

16. A method according to claim 1 wherein the soft tip is formed of polyurethane.

17. A method according to claim 1 wherein the core is formed of acetal.

18. A method according to claim 1 wherein said catheter body is extruded over the core prior to said step of forming a taper on the catheter body.

19. A method according to claim 18 wherein the core has been covered with a polymeric coating prior to extrusion of the catheter body thereover.

20. A method according to claim 1 wherein said step of applying pressure to the volume of material further includes substantially changing the shape of the volume of material.

21. A method according to claim 20 wherein said step of substantially changing the shape of the volume of material functions to form the length of the soft tip.

22. A method according to claim 1 wherein said step of forming a soft tip on the catheter body includes heating at least a portion of the volume of material.

23. A method according to claim 22 wherein said step of heating the volume of material further includes heating the entire volume of material and the taper.

24. A method according to claim 23 wherein said step of heating the entire volume of material further includes melting the entire volume of material.

25. A method according to claim 8 wherein said step of applying pressure to said predetermined volume of material occurs after said step of applying heat to said predetermined volume of material and after the predetermined volume of material begins to wick up the taper of the catheter body.

26. A method according to claim 1 wherein the core is formed of a lubricious polymer.

27. A method according to claim 26 wherein the lubricious polymer comprises acetal.

28. A method according to claim 19 wherein the polymeric coating is polytetrafluoroethylene.

29. A method according to claim 19 wherein the polymeric coating is adhesively bonded to the core.

30. A method according to claim 19 wherein the polymeric coating is etched on its exterior surface and becomes bonded to the catheter body when the catheter body is extruded thereover.

31. A method according to claim 30 wherein the polymeric coating is polytetrafluoroethylene.

32. A method according to claim 31 wherein the core comprises acetal.

* * * * *